United States Patent
Anderson et al.

(10) Patent No.: US 9,526,253 B2
(45) Date of Patent: *Dec. 27, 2016

(54) LIQUID ANIMAL REPELLANT CONTAINING OILS OF BLACK PEPPER AND CAPSICUM

(71) Applicant: Woodstream Corporation, Lititz, PA (US)

(72) Inventors: David L. Anderson, Lititz, PA (US); Theodore L. Davidson, St. Basile (CA)

(73) Assignee: WOODSTREAM CORPORATION, Lititz, PA (US)

(*) Notice: Subject to any disclaimer, the term of this patent is extended or adjusted under 35 U.S.C. 154(b) by 290 days.

This patent is subject to a terminal disclaimer.

(21) Appl. No.: 14/188,839

(22) Filed: Feb. 25, 2014

(65) Prior Publication Data

US 2014/0234446 A1     Aug. 21, 2014

Related U.S. Application Data

(63) Continuation of application No. 12/801,656, filed on Jun. 18, 2010, now abandoned, which is a continuation of application No. 10/938,522, filed on Sep. 13, 2004, now abandoned.

(51) Int. Cl.
*A01N 65/38* (2009.01)
*A01N 65/00* (2009.01)
*A01N 65/08* (2009.01)
*A01N 65/22* (2009.01)

(52) U.S. Cl.
CPC ............ *A01N 65/38* (2013.01); *A01N 65/00* (2013.01); *A01N 65/08* (2013.01); *A01N 65/22* (2013.01)

(58) Field of Classification Search
CPC ........ A01N 65/00; A01N 65/22; A01N 25/02; A01N 25/22; A01N 25/24; A01N 25/30; A01N 65/08; A01N 65/38; A01N 2300/00
See application file for complete search history.

(56) References Cited

U.S. PATENT DOCUMENTS

| | | | |
|---|---|---|---|
| 3,671,637 A | 6/1972 | Knowles |
| 3,877,979 A | 4/1975 | Clark |
| 4,148,891 A | 4/1979 | Smink |
| 4,795,637 A | 1/1989 | Harding, Jr. |
| 4,820,517 A | 4/1989 | Pfeiffer et al. |
| 4,943,389 A | 7/1990 | Weete et al. |
| 4,961,929 A | 10/1990 | Gurvich et al. |
| 5,045,536 A | 9/1991 | Baker |
| 5,698,191 A | 12/1997 | Wiersma et al. |
| 5,700,473 A | 12/1997 | Puritch et al. |
| 5,849,364 A | 12/1998 | Nachtman et al. |
| 6,159,474 A | 12/2000 | Davidson |
| 6,683,030 B2 | 1/2004 | Kober et al. |

FOREIGN PATENT DOCUMENTS

| | | |
|---|---|---|
| CA | 2148338 | 11/1996 |
| GB | 2213724 | 8/1989 |

*Primary Examiner* — Kyle Purdy
(74) *Attorney, Agent, or Firm* — Jacobson Holman, PLLC.

(57) ABSTRACT

The present invention provides a novel liquid animal repellent composition which is environmentally safe, non-toxic, long-lasting and efficacious against a wide of animals such as dogs, cats, raccoons, skunks, mice, rats, squirrels, chipmunks, deer, etc.

13 Claims, No Drawings

LIQUID ANIMAL REPELLANT CONTAINING OILS OF BLACK PEPPER AND CAPSICUM

This is a continuation of application Ser. No. 12/801,656 filed Jun. 18, 2010, which is a continuation of application Ser. No. 10/938,522 filed Sep. 13, 2004, the disclosures of which are incorporated herein by reference.

BACKGROUND OF THE INVENTION

1. Field of Invention

The present invention relates to liquid repellent compositions, a method of repelling animals and a method of manufacture of a repellent composition.

2. Description of Prior Art

Various types of repellent compositions are well known in the art. The nature of the repellent composition will vary depending upon the species of animal, bird or insect which it is intended to repel. Many of the known repellents are based on man made chemicals and for this reason, are not considered desirable for ecological reasons. Many repellent compositions have also been proposed which are environmentally friendly in that they utilize naturally occurring ingredients. Among such repellents are those shown in U.S. Pat. No. 4,455,304 which teaches the use of a composition for repelling birds. This bird repelling composition includes a finely divided garlic constituent and a finely divided cayenne pepper constituent. The patentee notes that neither black pepper nor white pepper is suitable for use. Similarly, U.S. Pat. No. 4,820,517 shows pepper extract has been also used as an insecticide.

U.S. Pat. No. 4,795,637 teaches the use of a rodent repellent powder which uses a thujone oil with a powder which can be selected from a number of different products including tobacco dust, pepper powder, sulphur powder, etc. The thujone oil is derived from the cedar tree and is a natural repellent.

More recently, U.S. Pat. No. 6,159,474 has shown that a composition providing a finely divided powder having essential oils of black pepper, capsicum and an oleoresin can be an effective repellent against a wide of animals such as dogs, cats, raccoons, skunks, mice, rats, squirrels, chipmunks, deer, etc. The disclosure in U.S. Pat. No. 6,159,474 is hereby incorporated by reference into this specification as if fully set forth in its entirety.

However, the dry repellent formula of U.S. Pat. No. 6,159,474 is limited in its application because can not be used on vertical or ceiling surfaces, applied difficult to reach locations, or utilized on surfaces where the granules can be hazardous, such as sidewalks, patios, paths, and other walkways.

Until the present invention, a liquid formulation of the composition of essential oils of black pepper, capsicum and an oleoresin was not successful. There were two major problems with making a liquid formulation. First was solubility. The essential oils and oleoresin do not ordinarily mix well in an aqueous solution. The inventors of the present invention succeeded in identifying appropriate emulsifiers and suspension agents that would solubilize the active ingredients and also be non-toxic and environmentally friendly.

Furthermore, the inventors also succeeded in creating a liquid repellent comprising the above essential oils and oleoresins together with one or more adhesive composition which surprisingly increased the longevity of the liquid formulation and made the invention useful in areas where the prior art dry only repellent was not effective.

Until now there has not been an adequate animal repellant formulation containing essential oils and oleoresins that was capable of being applied as a liquid and was also environmentally safe and non-toxic.

SUMMARY OF THE INVENTION

It is an object of the present invention to provide a liquid repellent which utilizes naturally occurring ingredients and has long-lasting effectiveness.

It is a further object of the present invention according to the preceding object and in which the naturally occurring ingredients are readily available.

It is another object of the present invention is provide a liquid repellent using naturally occurring ingredients and which repellent is effective against animals and which repellent has minimal toxicity.

It is a still further object of the present invention to provide a method for naturally repelling both domestic and other animals having an olfactory capability.

It is a further object of the present invention to provide a method of manufacture of a repellent having relatively non-toxic ingredients which can be readily carried out at a reasonable cost.

It is yet another object of the present invention to provide a liquid repellent which is long lasting, environmentally friendly and can be applied to surfaces not readily susceptible to treatment by the prior art dry only repellent.

According to one aspect of the present invention, there is provided a liquid repellent composition comprising between about 0.05% and about 2% by weight of an essential oil component selected from the group consisting of the essential oils of black pepper and the essential oil of capsicum, between about 0.1% and about 10% by weight of an oleoresin component selected from the group consisting of the oleoresins of black pepper and capsicum, an antioxidant in an amount sufficient to stabilize the oleoresin and essential oil, an effective amount of an emulsifier, a thickening agent, an adhesive, and the remainder water.

In an alternate embodiment, the present invention provides a liquid repellent composition comprising between about 0.05% to about 2% by weight of an essential oil selected from the group consisting of the essential oils of black pepper and capsicum, between about 0.1% and about 10% by weight of an oleoresin component selected from the group consisting of the oleoresins of black pepper and capsicum and between about 0.1% and about 10% by weight of an oleoresin of rosemary as an antioxidant in an amount sufficient to stabilize the oleoresin and essential oil, an effective amount of an emulsifier selected from the group consisting of glycerol monostearate, Mapeg®, polysorbate 80 and Atmos® 300, Kelgum® as a thickening agent, a polyvinyl acetate adhesive, and the remainder water.

It has been surprisingly found that a liquid repellent composition of the type described which incorporates an appropriate adhesive or other composition providing adhesive properties not only retains the liquid repellent composition effectively on contacted surfaces but also extends residual repellent power over extended periods of time. Adhesives known or believed to be effective for the present invention include polyvinyl acetate adhesives, glues such as Elmer's® glue and Titebond II®, and latex polymer adhesives. Other compositions include latex paint and the like. Water-soluble polyvinyl acetate adhesives are preferred for the present invention.

These and other objects of the present invention, as well as many of the attendant advantages thereof, will become more readily apparent when reference is made to the following detailed description of the preferred embodiments.

DETAILED DESCRIPTION AND PREFERRED EMBODIMENTS

In describing a preferred embodiment of the invention specific terminology will be resorted to for the sake of clarity. However, the invention is not intended to be limited to the specific terms so selected, and it is to be understood that each specific term includes all technical equivalents which operate in a similar manner to accomplish a similar purpose.

In its broadest aspects, the liquid repellent of the present invention is adapted to be used for a wide variety of animal species. As such, for the animal species, it can be utilized for both domestic and wild animals which have an olfactory capability, including such animals as dogs, cats, deer, skunks, raccoons, groundhogs, gophers, etc. Use of the repellent has also been found to be effective against some species of birds, including, for example, pigeons, geese, etc.

The composition utilizes, in combination, two different active ingredients; an oleoresin selected from the group consisting of black pepper and capsicum, and an essential oil of either black pepper or capsicum. Black pepper is classified as the genus *Piper*, species *Piper Nigrum*, and is the product of a shrub grown in a hot climate. The plant bears a small berry which is picked before it ripens and then dried.

The chemical compound which is responsible for the black pepper flavor is piperine. Piperine is soluble in alcohol, chloroform, ether, benzene and water. Piperine is not very reactive unless in a solution.

The present invention may use two components of the black pepper, both of which are commercially available. Thus, the present invention may utilize, as two of the chemically active ingredients, an oleoresin selected from the group consisting of black pepper and capsicum, and also an essential oil of either black pepper or capsicum.

In discovery of the formulation of the present invention, two problems in the art had to be overcome. The first problem to be overcome was the solubility of the essential oils and oleoresins in water. Since these materials do not mix easily, appropriate emulsifiers and suspending agents needed to be identified. This was particularly difficult with concentrate formulations where the essential oil and oleoresin contents are high. The second problem was trying to increase the effectiveness and longevity of the product. The prior art dry product used lard to keep the oils from volatilizing. Lard will not work in a liquid formulation.

The amount of the essential oil and oleoresin components may be varied and it is well within the skill of one knowledgeable in the art to so do. In preferred embodiments of the invention, the oleoresin will be present in an amount of between about 0.1 to about 10% by weight of the composition and preferably between about 0.25% and about 2.25% in even more preferred embodiments, would be present in a range of between about 1.0% and about 1.5% by weight. The oleoresin preferably has at least about 500,000 scoville heat units and more preferably in excess of about 1,000,000 scoville heat units. The essential oil is preferably present in a weight percentage of between about 0.05 and about 2% or preferably between about 0.1% and about 0.75% and even more preferably, between about 0.4% and about 0.6% by weight.

Preferred embodiments of the invention include the Use of other components in the composition. Thus, in one preferred embodiment, one may add the oleoresin of rosemary. Rosemary is an evergreen shrub of the mint family Labiatae and is classified as genus *Rosmarinus* species *Rosmarinus Officinalis*. The plant is widely used as an herb and is also used in perfumes. The use of the oleoresin of rosemary is desirable for providing a longer lasting effect to the repellent composition. In this respect, the oleoresin of rosemary functions as an antioxidant to stabilize the oleoresins and essential oils. For example, the oleoresin of black pepper will normally oxidize within 2 weeks if it is not stabilized.

The percentage of the oleoresin of rosemary should be used in an amount sufficient to perform its function as an antioxidant while too large an amount of rosemary will tend to neutralize the active repellent components. In general, the oleoresin of rosemary would be present in an amount of between about 0.01% and about 0.25% by weight and most preferably is present in an amount of between about 0.04% and about 0.07% by weight.

Without being limited to any particular theory, the composition of the present invention appears to act on the sinuses of the animal. In particular, it is believed that the essential oils provide an olfactory deterrent. Should the animal then attempt to taste the material, the oleoresins of capsicum and black pepper will reinforce the linkage between the smell and the undesirability of the same.

To assist in solubilizing the essential oils, the present invention provides soybean oil in a range of about 2% to about 7% by weight. Other oils may be substituted for soybean oil, such as corn oil, mineral, oil, rapeseed oil, sunflower oil, fish oil, cottonseed oil, linseed oil, sesame oil, peanut oil, olive oil, safflower oil or other similar oils.

Glycerol monostearate, Mapeg®, polysorbate 80, and Atmos® 300 are emulsifiers. Mapeg® is a mixture of polyethylene glycol esters of mono- and di-esters of various fatty acids. Atmos® 300 is also a mixture of mono- and di-esters of various fatty acids. Polysorbate 80 is otherwise known as polyoxyethylene sorbitan monooleate. Emulsifiers offer graduated hydrophilic to lipophilic surface active properties which make them useful as primary and secondary emulsifiers with stability over a wide range of formulating conditions. Lecithin may also be used as a natural emulsifier. It will be recognized by those skilled in the art that compositions such as polysorbate 80 or Mapeg® can be substituted by other similar formulations of esters of fatty acids.

Thickening agents provide bulk by gelling or thickening the solution. Kelgum® is a mixture of xanthan gum and locust bean gum which is often used in thickening food products such as processed cheeses, cottage cheese, dressings, aspics and pâtés.

Adhesives are used in the various embodiments of the present invention to help bind the formulation onto the surfaces it is sprayed on. This helps the formulation adhere to the sprayed surfaces and last longer in repelling animals in a specific area. Many different types of adhesives or glues can be used in the present invention. For example, glues such as Elmer's® Glue and Titebond II® can be used in a range of about 1% to about 20% by weight and preferably between about 8% and about 10% by weight for a ready-to-use product. Water-soluble polyvinyl acetate adhesives are the preferred adhesives, also in a range of about 1% to about 20% by weight in the ready-to-use product, preferably between about 8% and about 10% by weight, and most preferably about 9% by weight.

The method of manufacturing the repellent can be accomplished as follows:

A. Premix 1

1) Heat oleoresin of black pepper to 80° C. until it forms a liquid;
2) Add emulsifiers such as glycerol monostearate and polysorbate 80;
3) Cool to 50° C. and then add remaining oil, oleoresins and thickening agents (if necessary);

B) Premix 2

1) Add water;
2) Add water-soluble polyvinyl acetate adhesive; and

C) Combine Premix 1 and Premix 2.

The compositions of the present invention may be dispensed in a conventional manner, and preferably from a standard pump-spray container. The composition is first shaken in applicator and then sprayed on the target. Alternatively the aqueous repellent composition may be packaged in a pressurized container such as a conventional aerosol can or the like, utilizing an expandable gas, such as carbon dioxide ($CO_2$) as a propellant in a well known manner. For optimum effectiveness, the repellent composition of this invention is sprayed directly on targeted area to the point of runoff, and allowed to dry. A second coat of repellent can be added.

The following examples will provide illustrations of the use of the invention.

EXAMPLE 1

Ready to use animal repellent was formulated in the following percentages by weight:

| | |
|---|---|
| Oil of black pepper | 0.5 |
| Oleoresin of black pepper (40% piperine) | 0.5 |
| Oleoresin of capsicum | 0.55 |
| Oleoresin of rosemary | 0.05 |
| polyvinyl acetate adhesive | 9.0 |
| Kelgum® | 0.07 |
| Mapeg® | 0.5 |
| Lecithin | 3.0 |
| Acetic acid | 0.6 |
| Soybean oil | 5.0 |
| Water | 80.23 |

The composition of Example 1 was manufactured as follows:

A. Premix 1

1) Soybean oil, Mapeg®, and lecithin are added together and mixed until the composition is uniform;
2) The remaining oils and oleoresins and are then added to the composition and mixing is continued until uniform.

B. Premix 2

1) The water and Kelgum® were combined and mixed until uniform
2) Water-soluble polyvinyl acetate adhesive is then added and the composition is again mixed until uniform.

C. Premix 1 and Premix 2 were then combined and mixing continued until uniform.

EXAMPLE 2

Ready to use animal repellent was formulated in the following percentages by weights:

| | |
|---|---|
| Oil of Black Pepper | 0.5 |
| Oleoresin of Black Pepper (40% piperine) | 0.5 |
| Oleoresin of Capsicum | 0.55 |
| Oleoresin of Rosemary | 0.05 |
| Polyvinyl acetate adhesive | 9.0 |
| Polysorbate 80 | 3.2 |
| Glycerol monostearate | 4.8 |
| Water | 81.4 |

The composition of Example 2 was manufactured as follows:

A. Premix 1

1) The oleoresin of black pepper was heated to 80° C. until it formed a liquid;
2) The glycerol monostearate and polysorbate 80 were then added and mixed until uniform;
3) The composition is then cooled to 50° C. and then the remaining oil, and oleoresins were added and mixed until uniform.

B. Premix 2

1) Water-soluble polyvinyl acetate adhesive is combined with the water component.

C. Combine Premix 1 and Premix 2.

EXAMPLE 3

Animal repellent concentrate was formulated in the following percentages by weight:

| | |
|---|---|
| Oil of Black Pepper | 4.0 |
| Oleoresin of Black Pepper (40% piperine) | 4.0 |
| Oleoresin of Capsicum | 4.4 |
| Oleoresin of Rosemary | 0.4 |
| Polyvinyl acetate adhesive | 19.0 |
| Polysorbate 80 | 5.6 |
| Glycerol monostearate | 8.4 |
| Water | 54.2 |

The composition of Example 3 was manufactured as follows:

A. Premix 1

1) The oleoresin of black pepper was heated to 80° C. until it formed a liquid;
2) The glycerol monostearate and polysorbate 80 were then added and mixed until uniform;
3) The composition is cooled to 50° C. and then the remaining oil, and oleoresins were added and mixed until uniform.

B. Premix 2

1) Water-soluble polyvinyl acetate adhesive is combined with the water component.

C. Combine Premix 1 and Premix 2.

Having described the invention, many modifications thereto will become apparent to those skilled in the art to which it pertains without deviation from the spirit of the invention as defined by the scope of the appended claims.

What is claimed is:

1. A sprayable liquid animal repellant composition comprising:

a) between about 0.05% and about 2% by weight of an essential oil component selected from the group consisting of the essential oil of black pepper, the essential oil of capsicum, and mixtures thereof;
b) between about 0.1% and about 10% by weight of an oleoresin component selected from the group consisting of the oleoresin of black pepper, the oleoresin of capsicum, and mixtures thereof;
c) an antioxidant in an amount sufficient to stabilize the oleoresin component and the essential oil component;
d) an effective amount of an emulsifier and an adhesive;
e) sufficient water so that the composition is sprayable, wherein the sprayable liquid animal repellant is free of lard and an oleoresin-solubilizing vegetable oil in an amount that fully solubilizes the oleoresin.

2. A sprayable liquid animal repellant composition comprising:
a) between about 0005% to about 2% by weight of an essential oil selected from the group consisting of the essential oil of black pepper, the essential oil of capsicum, and mixtures thereof;
b) between about 0.1% and about 10% by weight of an oleoresin selected from the group consisting of the oleoresin of black pepper, the oleoresin of capsicum, and mixtures thereof;
c) between about 0.1% and about 10% by weight of an antioxidant in an amount sufficient to stabilize the oleoresin component and the essential oil component;
d) an effective amount of an emulsifier selected from the group consisting of glycerol monostearate, a mixture of mono- and di-esters of various fatty acids, a mixture of polyethylene glycol esters of mono- and di-esters of various fatty acids, and polyoxyethylene sorbitan monooleate; and
e) an effective amount a polyvinyl adhesive; and
f) sufficient water so that the composition is sprayable; wherein the sprayable liquid animal repellant is free of lard and an oleoresin-solubilizing vegetable oil in an amount that fully solubilizes the oleoresin.

3. The sprayable liquid animal repellent composition of claim 1, wherein said oleoresin component comprises between about 0.25% and about 2.25% by weight.

4. The sprayable liquid animal repellent composition of claim 1, wherein said oleoresin component comprises between about 1.0% and about 1.5% by weight.

5. The composition of claim 1, wherein said essential oil is present in an amount of between about 0.1% and about 0.75% by weight.

6. The composition of claim 2, wherein said antioxidant is oleoresin of rosemary being present in an amount of between 0.01% and 0.25% by weight.

7. The composition of claim 6, wherein said oleoresin of rosemary is present in an amount of between 0.04% and 0.07% by weight.

8. The composition of claim 1, wherein said oleoresin of capsicum has a minimum of 500,000 scoville heat units.

9. The composition of claim 2, wherein said oleoresin of capsicum has a minimum of 500,000 scoville heat units.

10. A sprayable, concentrated liquid animal repellant composition comprising: 4% by weight of oil of black pepper, 4% by weight of oleoresin of black pepper (40% piperine), 4.4% by weight of oleoresin of capsicum, 0.4% by weight of oleoresin of rosemary, 19% by weight of a water-soluble polyvinyl acetate adhesive, 7% by weight of polyoxyethylene sorbitan monooleate, 7% by weight of glycerol monostearate, and 54.2% by weight of water, wherein the sprayable liquid animal repellant is free of lard and an oleoresin-solubilizing vegetable oil in an amount that solubilizes the oleoresin.

11. A method of manufacturing a liquid animal repellent composition of claim 1, comprising the steps of:
a) adding soybean oil, a mixture of polyethylene glycol esters of mono- and di-esters of various fatty acids, and lecithin together and mixing until the composition is uniform;
b) adding the remaining oils and oleoresins to the mixture of step a) and continuing mixing until uniform;
c) combining the water and a mixture of xanthan gum and locust bean gum separately and mixing until uniform;
d) adding a polyvinyl adhesive to the mixture of step c) and continuing mixing until uniform; and
e) combining the mixtures from steps b) and d) and continuing mixing until uniform.

12. A method of manufacturing a liquid animal repellent composition of claim 1, comprising the steps of:
a) heating the oleoresin of black pepper to about 80° C. until it forms a liquid;
b) adding glycerol monostearate and polyoxyethylene sorbitan monooleate to the mixture of step a) and mixing until uniform;
c) cooling the mixture to 50° C. and adding the remaining oil, and oleoresins to the mixture of step b) and continuing mixing until uniform;
d) combining separately, a polyvinyl adhesive with the water component; and
e) adding the mixture from step c) to the mixture from step d) and continuing mixing until uniform.

13. A method for repelling animals, the method comprising the steps of applying to an area to be protected an effective amount to repel a desired animal of a liquid animal repellant composition of claim 1.

* * * * *